(12) United States Patent
Suzuki

(10) Patent No.: US 7,893,275 B2
(45) Date of Patent: Feb. 22, 2011

(54) POLYCYCLIC KETONE COMPOUND AND PROCESS FOR PRODUCING THE SAME

(75) Inventor: Keisuke Suzuki, Yokohama (JP)

(73) Assignee: Japan Science and Technology Agency, Saitama (JP)

( * ) Notice: Subject to any disclaimer, the term of this patent is extended or adjusted under 35 U.S.C. 154(b) by 1049 days.

(21) Appl. No.: 10/591,974

(22) PCT Filed: Mar. 10, 2005

(86) PCT No.: PCT/JP2005/004723

§ 371 (c)(1),
(2), (4) Date: Sep. 8, 2006

(87) PCT Pub. No.: WO2005/095422

PCT Pub. Date: Oct. 13, 2005

(65) Prior Publication Data

US 2007/0149786 A1    Jun. 28, 2007

(30) Foreign Application Priority Data

Mar. 10, 2004  (JP)  ............... 2004-067741

(51) Int. Cl.
C07D 261/20   (2006.01)

(52) U.S. Cl. .................................. 548/241

(58) Field of Classification Search ............ None
See application file for complete search history.

(56) References Cited

U.S. PATENT DOCUMENTS

| 4,101,327 A | 7/1978 | Frass |
| 2003/0073732 A1 | 4/2003 | Sakata et al. |
| 2004/0028660 A1 | 2/2004 | Hariri et al. |
| 2004/0034084 A1 | 2/2004 | Zeldis |
| 2004/0092562 A1 | 5/2004 | Sakata et al. |

FOREIGN PATENT DOCUMENTS

| GB | 1576217 | | 10/1980 |
| JP | 52-82415 A | | 7/1977 |
| JP | 52-83369 A | | 7/1977 |
| JP | 2004-143082 | * | 5/2004 |
| JP | 2004-143082 A | | 5/2004 |
| WO | WO 02/066450 A2 | | 8/2002 |
| WO | WO 03/099221 A2 | | 12/2003 |
| WO | WO 03/102151 A2 | | 12/2003 |

OTHER PUBLICATIONS

Hachisu et al. "Catalytic Intramolecular Crossed Aldehyde-Ketone Benzoin Reactions: A Novel Synthesis of Functionalized Preanthraquinones." J. Am. Chem. Soc., 2003, 125 (28), pp. 8432-8433.*
JP 2004-143082, Machine translation. Obtained from URL: http://www.ipdl.inpit.go.jp/homepg_e.ipdl Accessed Jun. 21, 2009.*
Bachman et al., Journal of the American Chemical Society, vol. 57, No. 6, Jun. 1935, pp. 1095-1098.*
Hachisu et al. J. Amer. Chem. Soc. 2003, 125, pp. 8432-8433.*
Supplementary European Search Report mailed Apr. 8, 2009, in corresponding European patent application No. 05720958, 3 pages.
Hachisu et al., "Catalytic Intramolecular Crossed Aldehyde-Ketone Benzoin Reactions: A Novel Synthesis of Functionalized Preanthraquinones," J. Am. Chem. Soc., Jul. 16, 2003, 125(28):8432-8433.

* cited by examiner

*Primary Examiner*—Rebecca L Anderson
*Assistant Examiner*—Alicia L Otton
(74) *Attorney, Agent, or Firm*—Foley & Lardner LLP

(57) ABSTRACT

The present application provides polycyclic ketone compounds that have a quarternary asymmetric carbon center and conform to Formula (I):

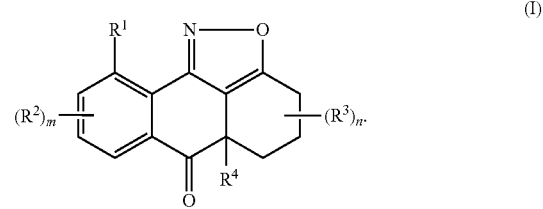

Also provided is a stereoselective method for synthesizing the polycyclic ketone compounds.

1 Claim, No Drawings

POLYCYCLIC KETONE COMPOUND AND PROCESS FOR PRODUCING THE SAME

FIELD OF THE INVENTION

The present invention relates to that addition of various alkylmetals to α-ketol selectively obtained provides adducts each corresponding to the compounds at a high stereoselectivity. Further, it relates to a synthetic process of a compound having an isoxazole skeleton and a polycyclic ketone compound having an anthraquinone skeleton and the like by transfer reaction under an acidic condition. The present invention relates to medical compounds, agricultural chemical compounds and dye compounds each comprising a polycyclic ketone compound and a production process for the same.

BACKGROUND OF THE INVENTION

Methods for synthesizing stereoselectively polycyclic compounds having a quaternary asymmetric carbon in an internuclear position are very few and have so far been scarcely known.

Polycyclic compounds are contained in physiologically active compounds and functional materials in many cases. For example, some substituted anthraquinone compound has so far been known as a dye. For example, compounds which have an amino group, an alkylamino group or an arylamino group in an α-position of anthraquinone and which have a sulfonic acid group in the other positions are publicly known as anthraquinone base acidic dyes. Specifically, Anthraquinone Iris R, Anthraquinone Violet RN, 3RN, Anthraquinone Blue RXO and Anthracyanine are produced and marketed as dyes. Applications as an antitumor agent and a photographic material are found for some kind of anthraquinone compounds.

Thus, polycyclic ketone compounds having an anthraquinone skeleton have various industrially useful applications, but so many synthetic processes which are satisfactory in terms of reaction conditions, a number of reaction steps and application ranges are not necessarily available. Accordingly, desired is a process for synthesizing stereoselectively polycyclic ketone compounds having various anthraquinone skeleton.

DISCLOSURE OF THE INVENTION

Various investigations repeated by the present inventors on a process for synthesizing a polycyclic ketone compound having an anthraquinone skeleton and the like have resulted in finding that polycyclic ketone compounds having an anthraquinone skeleton and the like which are observed in, for example, physiologically active natural organic compounds can be stereoselectively synthesized at a high yield.

That is, the first embodiment of the present invention is a production process for producing a polycyclic ketone compound represented by the following Formula (I):

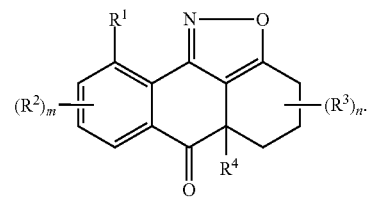

(I)

(wherein $R^1$ represents a hydrogen atom, a hydroxyl group, a halogen atom, a silyloxy group which may be substituted, a $C_1$ to $C_{10}$ alkoxy group which may be substituted or a $C_1$ to $C_{20}$ hydrocarbon group which may be substituted;

$R^2$ may be independent from each other and the same as or different from each other and represents a halogen atom, a hydroxyl group, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{20}$ hydrocarbon group which may be substituted or a heterocyclic group of a 5- to 7-membered ring which may be substituted or two groups of $R^2$ form a hydrocarbon group of a 4- to 6-membered ring which may be substituted together with adjacent carbon atoms;

$R^3$ may be independent from each other and the same as or different from each other and represents a halogen atom, a hydroxyl group, a $C_1$ to $C_{10}$ alkoxycarbonyl group which may be substituted or a $C_6$ to $C_{20}$ hydrocarbon group which may be substituted or two groups of $R^3$ form a hydrocarbon group of a 4- to 6-membered ring which may be substituted together with adjacent carbon atoms;

$R^4$ represents a hydrogen atom, a halogen atom, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{10}$ alkyl group which may be substituted, a phenyl group which may be substituted or a $C_1$ to $C_{20}$ hydrocarbon group which may be substituted;

m represents an integer of 0 to 3; and n represents an integer of 0 to 6), wherein a compound represented by the following Formula (IIa) or (IIb) is treated under an acidic condition:

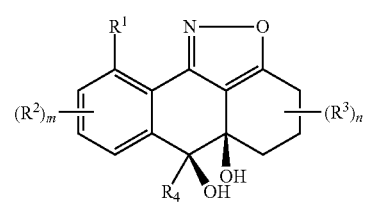

(IIa)

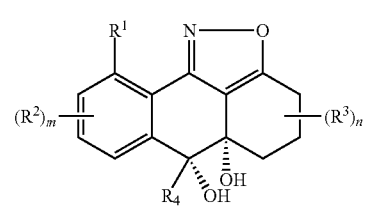

(IIb)

(wherein $R^1$, $R^2$, $R^3$, $R^4$, m and n are the same as described above).

The treatment described above in the first embodiment of the present invention is carried out preferably under the presence of a catalyst. The catalyst is selected preferably from Lewis acids, protonic acids and mixtures thereof. The protonic acid described above is selected preferably from mineral acids such as hydrogen chloride, alkanesulfonic acids, carboxylic acids and mixtures thereof. The alkanesulfonic acid described above is preferably trifluoromethanesulfonic acid ($CF_3O_3HS$)

In the first embodiment of the present invention, the treatment is preferably carried out at a temperature of −78 to 150° C. for 0.1 to 50 hours, and the treatment is more preferably carried out at a temperature of −30 to 40° C. for 1 to 20 hours.

In the first embodiment of the present invention, the solvent described above is selected preferably from methanol, ethanol, tetrahydrofuran, diethyl ether, dichloromethane, chloroethylene, dichloroethylene, chloroform, benzene, toluene, acetonitrile, N,N-dimethylformamide and dimethyl ketone, water, 1,4-dioxane, 1,2-dimethoxyethane and mixtures thereof.

The second embodiment of the present invention is a production process for producing a compound represented by the following Formula (IIa) or (IIb):

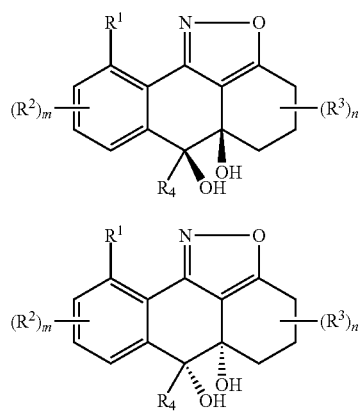

(wherein $R^1$, $R^2$, $R^3$, $R^4$, m and n are the same as described below) using a production process comprising treating a compound represented by the following Formula (III):

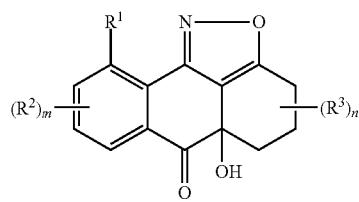

(wherein $R^1$ represents a hydrogen atom, a hydroxyl group, a halogen atom, a silyloxy group which may be substituted, a $C_1$ to $C_{10}$ alkoxy group which may be substituted or a $C_1$ to $C_{20}$ hydrocarbon group which may be substituted;

$R^2$ may be independent from each other and the same as or different from each other and represents a halogen atom, a hydroxyl group, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{20}$ hydrocarbon group which may be substituted or a heterocyclic group of a 5- to 7-membered ring which may be substituted or two groups of $R^2$ form a hydrocarbon group of a 4- to 6-membered ring which may be substituted together with adjacent carbon atoms;

$R^3$ may be independent from each other and the same as or different from each other and represents a halogen atom, a hydroxyl group, a $C_1$ to $C_{10}$ alkoxycarbonyl group which may be substituted or a $C_6$ to $C_{20}$ hydrocarbon group which may be substituted or two groups of $R^3$ form a hydrocarbon group of a 4- to 6-membered ring which may be substituted together with adjacent carbon atoms;

m represents an integer of 0 to 3; and n represents an integer of 0 to 6) under the presence of a compound represented by the following Formula (IV):

(wherein M represents metal, and $R^4$ represents a hydrogen atom, a halogen atom, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{10}$ alkyl group which may be substituted, a phenyl group which may be substituted or a $C_1$ to $C_{20}$ hydrocarbon group which may be substituted).

In the second embodiment of the present invention, the compound represented by Formula (IIa) or (IIb) described above (wherein $R^1$, $R^2$, $R^3$, $R^4$, m and n are the same as described above) is obtained in the form of a single isomer.

In the second embodiment of the present invention, the compound represented by Formula (IIa) or (IIb) described above (wherein $R^1$, $R^2$, $R^3$, $R^4$, m and n are the same as described above) is preferably treated at a temperature of −120 to 40° C. for 0.01 to 5 hours, more preferably at a temperature of −100 to −20° C. for 0.05 to 1 hour, whereby it is produced.

In the second embodiment of the present invention, provided is a production process in which the solvent described above used in the treatment for producing the compound represented by Formula (IIa) or (IIb) described above (wherein $R^1$, $R^2$, $R^3$, $R^4$, m and n are the same as described above) is selected from methanol, ethanol, tetrahydrofuran, diethyl ether, dichloromethane, chloroethylene, dichloroethylene, chloroform, benzene, toluene, acetonitrile, N,N-dimethylformamide and dimethyl ketone, water, 1,4-dioxane, 1,2-dimethoxyethane and mixtures thereof.

The third embodiment of the present invention is a polycyclic ketone compound represented by the following Formula (I):

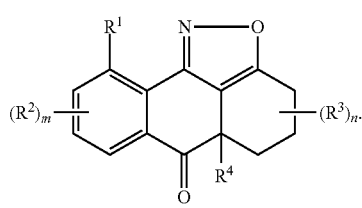

(wherein $R^1$ represents a hydrogen atom, a hydroxyl group, a halogen atom, a silyloxy group which may be substituted, a $C_1$ to $C_{10}$ alkoxy group which may be substituted or a $C_1$ to $C_{20}$ hydrocarbon group which may be substituted;

$R^2$ may be independent from each other and the same as or different from each other and represents a halogen atom, a hydroxyl group, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{20}$ hydrocarbon group which may be substituted or a heterocyclic group of a 5- to 7-membered ring which may be substituted or two groups of $R^2$ form a hydrocarbon group of a 4- to 6-membered ring which may be substituted together with adjacent carbon atoms;

$R^3$ may be independent from each other and the same as or different from each other and represents a halogen atom, a hydroxyl group, a $C_1$ to $C_{10}$ alkoxycarbonyl group which may be substituted or a $C_6$ to $C_{20}$ hydrocarbon group which may be substituted or two groups of $R^3$ form a hydrocarbon group of a 4- to 6-membered ring which may be substituted together with adjacent carbon atoms;

$R^4$ represents a hydrogen atom, a halogen atom, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{10}$ alkyl group which may be substituted, a phenyl group which may be substituted or a $C_1$ to $C_{20}$ hydrocarbon group which may be substituted; m represents an integer of 0 to 2; and n represents an integer of 0 to 4).

The fourth embodiment of the present invention is a polycyclic compound represented by the following Formula (IIa) or (IIb):

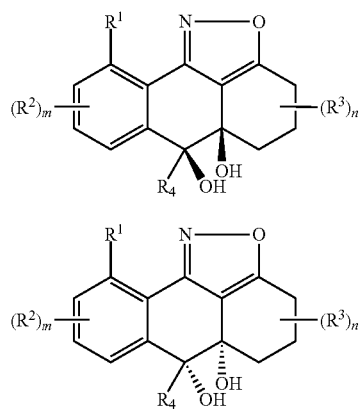

(wherein $R^1$ represents a hydrogen atom, a hydroxyl group, a halogen atom, a silyloxy group which may be substituted, a $C_1$ to $C_{10}$ alkoxy group which may be substituted or a $C_1$ to $C_{20}$ hydrocarbon group which may be substituted;

$R^2$ may be independent from each other and the same as or different from each other and represents a halogen atom, a hydroxyl group, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{20}$ hydrocarbon group which may be substituted or a heterocyclic group of a 5- to 7-membered ring which may be substituted or two groups of $R^2$ form a hydrocarbon group of a 4- to 6-membered ring which may be substituted together with adjacent carbon atoms;

$R^3$ may be independent from each other and the same as or different from each other and represents a halogen atom, a hydroxyl group, a $C_1$ to $C_{10}$ alkoxycarbonyl group which may be substituted or a $C_6$ to $C_{20}$ hydrocarbon group which may be substituted or two groups of $R^3$ form a hydrocarbon group of a 4- to 6-membered ring which may be substituted together with adjacent carbon atoms;

$R^4$ represents a hydrogen atom, a halogen atom, a cyano group, a nitro group, an amino group which may be substituted, a $C_1$ to $C_{10}$ alkoxy group which may be substituted, a $C_1$ to $C_{10}$ acyl group which may be substituted, a $C_1$ to $C_{10}$ alkyl group which may be substituted, a phenyl group which may be substituted or a $C_1$ to $C_{20}$ hydrocarbon group which may be substituted; m represents an integer of 0 to 2; and n represents an integer of 0 to 4).

In the present invention, $R^1$ is preferably a hydrogen atom, a hydroxyl group, a halogen atom, a silyloxy group which may be substitute or a $C_1$ to $C_{10}$ alkoxy group which may be substituted; it is more preferably a hydrogen atom, a hydroxyl group, a halogen atom, a silyloxy group which may be substitute, a $C_1$ to $C_5$ alkoxy group or a $C_1$ to $C_5$ alkoxy $C_1$ to $C_5$ alkoxy group; and it is further preferably a hydroxyl group, a halogen atom, a silyloxy group which may be substitute, methoxy or methoxymethoxy.

In the present invention, preferably $R^2$ may be independent from each other and the same as or different from each other and represents a halogen atom, a hydroxyl group, a cyano group, a nitro group, an amino group which may be substituted, a $C_1$ to $C_{20}$ hydrocarbon group which may be substituted, a $C_1$ to $C_{10}$ alkoxy group which may be substituted or a $C_1$ to $C_{10}$ acyl group which may be substituted or two groups of $R^2$ form a hydrocarbon group of a 5- to 6-membered ring which may be substituted together with adjacent carbon atoms; more preferably it may be independent from each other and the same as or different from each other and represents a halogen atom, a hydroxyl group, a cyano group, a nitro group, an amino group which may be substituted, a $C_1$ to $C_{10}$ alkyl group which may be substituted or a $C_1$ to $C_{10}$ alkoxy group which may be substituted or two groups of $R^2$ form a hydrocarbon group of a 6-membered ring together with adjacent carbon atoms; and further preferably it may be independent from each other and the same as or different from each other and represents a halogen atom, a hydroxyl group, a cyano group, a nitro group, an amino group, a $C_1$ to $C_3$ alkyl group or a $C_1$ to $C_3$ alkoxy group which may be substituted or two groups of $R^2$ form a condensed benzene ring together with adjacent carbon atoms.

In the present invention, preferably $R^3$ may be independent from each other and the same as or different from each other and represents a halogen atom, a hydroxyl group or a $C_1$ to $C_{10}$ alkoxycarbonyl group which may be substituted or a $C_1$ to $C_{10}$ alkyl group which may be substituted or two groups of $R^3$ form a hydrocarbon group of a 5- to 6-membered ring which may be substituted together with adjacent carbon atoms; more preferably it may be independent from each other and the same as or different from each other and represents a halogen atom, a hydroxyl group or a $C_1$ to $C_{10}$ alkyl group which may be substituted or two groups of $R^3$ form a hydrocarbon group of a 6-membered ring together with adjacent carbon atoms; and further preferably it may be independent from each other and the same as or different from each other and represents a halogen atom, a hydroxyl group or a $C_1$ to $C_3$ alkyl group which may be substituted or two groups of $R^3$ form a condensed cyclohexyl ring together with adjacent carbon atoms.

In the present invention, $R^4$ is preferably a hydrogen atom, a halogen atom, an amino group which may be substituted, a $C_1$ to $C_{10}$ alkoxy group which may be substituted, a $C_1$ to $C_{10}$ acyl group which may be substituted, a $C_1$ to $C_{10}$ alkyl group which may be substituted, a $C_1$ to $C_{10}$ alkenyl group which may be substituted, a $C_1$ to $C_{10}$ alkynyl group which may be substituted or a phenyl group which may be substituted; it is more preferably a hydrogen atom, a halogen atom, an amino group which may be substituted, a $C_1$ to $C_5$ alkoxy group which may be substituted, a $C_1$ to $C_5$ acyl group which may be substituted, a $C_1$ to $C_5$ alkyl group which may be substituted, a $C_1$ to $C_5$ alkenyl group which may be substituted, a $C_1$ to $C_5$ alkynyl group which may be substituted or a phenyl group which may be substituted; and it is further preferably a $C_1$ to $C_3$ alkyl group which may be substituted, a vinyl group, a phenyl group or a tolyl group.

In the present invention, M is preferably metal such as lithium, magnesium, sodium, potassium or zinc.

In the present invention, m is, to be specific, an integer of 0 to 2; and it is more specifically 0 or 1. To be specific, n is an integer of 0 to 4; to be more specific, it is an integer of 0 to 3; and to be further specific, it is 0 or 1.

In the present specification, the "$C_1$ to $C_{20}$ hydrocarbon group" means a hydrocarbon group which may be saturated or unsaturated acyclic or may be saturated or unsaturated cyclic. When it is acyclic, it may be either linear or branched. The $C_1$ to $C_{20}$ hydrocarbon group includes, for example, a $C_1$ to $C_{20}$ alkyl group, a $C_2$ to $C_{20}$ alkenyl group, a $C_2$ to $C_{20}$ alkynyl group, a $C_3$ to $C_{20}$ allyl group, a $C_4$ to $C_{20}$ alkyldienyl group, a $C_4$ to $C_{20}$ polyenyl group, a $C_6$ to $C_{18}$ aryl group, a $C_6$ to $C_{20}$ alkylaryl group, a $C_6$ to $C_{20}$ arylalkyl group, a $C_4$ to $C_{20}$ cycloalkyl group, a $C_4$ to $C_{20}$ cycloalkenyl group and a ($C_3$ to $C_{10}$ cycloalkyl) $C_1$ to $C_{10}$ alkyl group.

The $C_1$ to $C_{20}$ hydrocarbon group used in the present invention includes, specifically, a $C_1$ to $C_{10}$ alkyl group, a $C_2$ to $C_{10}$ alkenyl group, a $C_2$ to $C_{10}$ alkynyl group, a $C_3$ to $C_{10}$ allyl group, a $C_4$ to $C_{10}$ alkyldienyl group, a $C_4$ to $C_{10}$ polyenyl group, a $C_6$ to $C_{10}$ aryl group, a $C_6$ to $C_{12}$ alkylaryl group, a $C_6$ to $C_{12}$ arylalkyl group, a $C_4$ to $C_{10}$ cycloalkyl group and a $C_4$ to $C_{10}$ cycloalkenyl group.

The "alkyl group" in the present specification is an alkyl group which may be either linear or branched, and it includes, for example, methyl, ethyl, propyl, n-butyl, t-butyl, pentyl and hexyl.

In the present specification, the "alkenyl group" includes a linear or branched alkenyl group having 1 to 3 double bonds and 2 to 10 carbon atoms, and it includes, to be specific, ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl and 2-decenyl.

The "alkynyl group" includes a linear or branched alkenyl group having 1 to 3 triple bonds and 2 to 10 carbon atoms, and it includes, to be specific, ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl and 2-decynyl.

The "cycloalkyl group" includes, for example, a cycloalkyl group having 3 to 10 carbon atoms, and it includes, to be specific, cyclopropyl, cyclobutyl, cyclopentyl, cyclohexyl and cycloheptyl. A lower cycloalkyl group includes a cycloalkyl group having 3 to 6 carbon atoms.

The "alkoxy group" means an oxy group to which an alkyl group is bonded and includes, to be specific, methoxy, ethoxy, propoxy, 2-propoxy, butoxy, 1,1-dimetylethoxy, pentoxy and hexoxy.

The "acyl group" includes, for example, formyl, acetyl, propanoyl, 2-propanoyl, pivaloyl, valeryl, pivaloyl, trifluoroacetyl, benzoyl, naphthoyl, nicotinoyl, methanesulfonyl, trifluoromethanesulfonyl and p-toluenesulfonyl.

The "aryl group" includes, for example, a phenyl group, a naphthyl group such as a 1-naphthyl group or a 2-naphthyl group, an indenyl group such as a 2-indenyl group, an anthryl group such as a 2-anthryl group, a tolyl group such as 2-tolyl, 3-tolyl and 4-tolyl and a biphenyl group.

The "silyloxy group" includes, for example, dimethylsilyloxy, diethylsilyloxy, trimethylsilyloxy, triethylsilyloxy, trimethoxysilyloxy, triethoxysilyloxy, diphenylmethylsilyloxy, triphenylsilyloxy, triphenoxysilyloxy, dimethylmethoxysilyloxy, dimethylphenoxysilylox and methylmethoxysilyloxy.

The "heterocyclic group" includes, for example, a saturated heterocyclic group or an unsaturated heterocyclic group of a 5- to 7-membered ring having 1 to 3 nitrogen atoms, an oxygen atom and/or a sulfur atom. The saturated heterocyclic group includes, for example, tetrahydrofuryl, pyrrolidinyl, pyrazolidinyl, imidazolidinyl, piperidinyl, morpholinyl, thiamorpholinyl and piperazinyl. The unsaturated heterocyclic group includes, for example, furyl, thienyl, indolyl and isothiazolyl.

The "hydrocarbon group of a 4- to 6-membered ring" includes, for example, cyclobutyl, cyclopentyl, cyclohexyl and phenyl.

Groups which can be substituted into a hydrocarbon group and a heterocyclic group include, for example, a halogen atom (for example, fluorine, chlorine, bromine and iodine), a nitro group, a cyano group, a $C_{1-6}$ alkyl group which may be halogenated, a $C_{3-6}$ cycloalkyl group which may be halogenated, a $C_{1-6}$ alkoxy group which may be halogenated, a $C_{1-6}$ alkylthio group which may be halogenated, a hydroxy group, an amino group, a mono-$C_{1-6}$ alkylamino group (for example, methylamino, ethylamino, propylamino, isopropylamino and butylamino), a di-$C_{1-6}$ alkylamino group (for example, dimethylamino, diethylamino, dipropylamino, dibutylamino and ethylmethylamino), a formyl group, a carboxy group, a carbamoyl group, a $C_{1-6}$ alkylcarbonyl group which may be halogenated, a $C_{1-6}$ alkoxycarbonyl group (for example, methoxycarbonyl, ethoxycarbonyl, propoxycarbonyl and tert-butoxycarbonyl), a mono-$C_{1-6}$ alkylcarbamoyl group (for example, methylcarbamoyl and ethylcarbamoyl), a di-$C_{1-6}$ alkylcarbamoyl group (for example, dimethylcarbamoyl, diethylcarbamoyl and ethylmethylcarbamoyl), a $C_{1-6}$ alkylsulfonyl group which may be halogenated, a formylamino group, a $C_{1-6}$ alkylcarboxamide group which may be halogenated, a $C_{1-6}$ alkoxycarboxamide group (for example, methoxycarboxamide, ethoxycarboxamide, propoxycarboxamide and butoxycarboxamide), a $C_{1-6}$ alkylsulfonylamino group (for example, methylsulfonylamino and ethylsulfonylamino), a $C_{1-6}$ alkylcarbonyloxy group (for example, acetoxy and propanoyloxy), a $C_{1-6}$ alkoxycarbonyloxy group (for example, methoxycarbonyloxy, ethoxycarbonyloxy, propoxycarbonyloxy and butoxycarbonyloxy), a mono-$C_{1-6}$ alkylcarbamoyloxy group (for example, methylcarbamoyloxy and ethylcarbamoyloxy) and a di-$C_{1-6}$ alkylcarbamoyloxy group (for example, dimethylcarbamoyloxy and diethylcarbamoyloxy). The number of the above substituents substituted shall not specifically be restricted, for example, 1 to 5 groups, more specifically 1 to 3 groups of the above substituents are substituted.

The reaction in the present invention can be allowed to catalytically proceed. According to the present invention, a polycyclic ketone compound provided with functional groups to a high degree can be provided, and it is useful for synthesizing particularly compounds having an aromatic ring and an alicyclic structure in combination.

Further, the reaction in the present invention is reaction having a high stereoselectivity, and therefore it has been found that asymmetric information in the starting material can be reflected on an optical purity of the final product.

BEST MODE FOR CARRYING OUT THE INVENTION

The production process of the present invention shall be explained below in more details.

The polycyclic compound of the present invention can be produced by a process shown in the following scheme 1.

Scheme 1

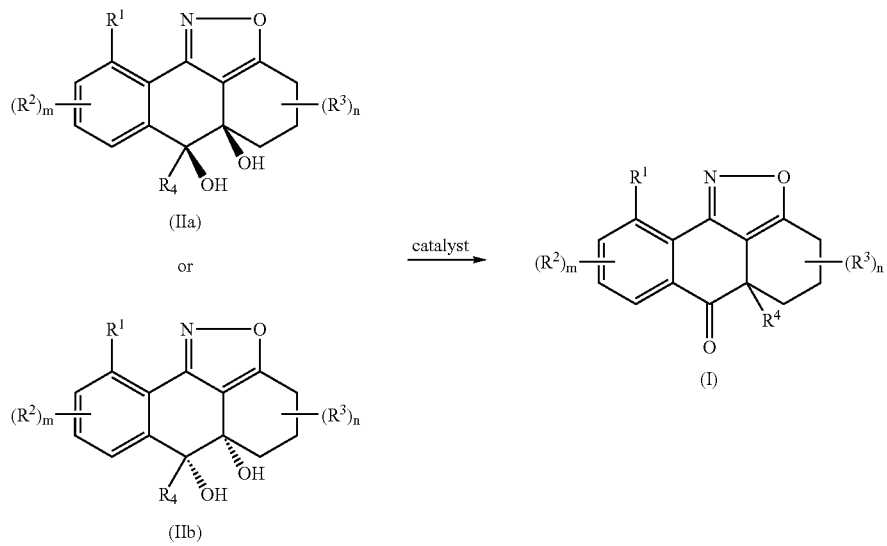

(wherein $R^1$, $R^2$, $R^3$, $R^4$, m and n show the same meanings as described above).

In the scheme 1 described above, transfer reaction such as a pinacol type proceeds by treating the compound represented by Formula (IIa) or (IIb) on an acidic condition in the presence of a catalyst, and obtained is the compound represented by Formula (I) in which a hydroxyl group in an internuclear position is substituted with an alkyl group. In this case, a direction in which $R_4$ is bonded can be determined by selecting either of Formula (IIa) and Formula (IIb).

The suited catalyst used here is preferably an acid. For example, the acid is selected preferably from Lewis acids, protonic acids and mixtures thereof. The protonic acid described above is selected preferably from mineral acids such as hydrogen chloride, alkanesulfonic acids, carboxylic acids and mixtures thereof. Trifluoromethanesulfonic acid is preferably used as the alkanesulfonic acid described above. A use amount of the acids described above is 0.05 to 0.4 mole, preferably 0.05 to 0.2 mole per mole of the compound represented by Formula (IIa) or (IIb) described above.

The above reaction is carried out in the absence of a solvent or in a solvent which is inactive to the reaction. The solvent which can be used in the above reaction and which is inactive to the reaction includes, for example, methanol, ethanol, tetrahydrofuran, diethyl ether, dichloromethane, chloroethylene, dichloroethylene, chloroform, benzene, toluene, acetonitrile, N,N-dimethylformamide and dimethyl ketone, water, 1,4-dioxane and 1,2-dimethoxyethane. They may be used by mixing two or more kinds thereof in a suitable proportion. Among the above solvents, 1,1-dichloroethylene is suitably used.

The reaction described above is carried out, for example, at a temperature of −78 to 150° C., preferably −30 to 40° C. for 0.1 to 50 hours, preferably 0.1 to 5 hours. This reaction is carried out usually at an atmospheric pressure, but it can be carried out, if necessary, under reduced pressure or applied pressure.

The intended compound of Formula (Ia) or (Ib) can be isolated, if necessary, from the reaction mixture thus obtained, for example, by separating means such as various chromatographies.

The compound represented by Formula (IIa) or (IIb) described above used in the above scheme 1 is publicly known or can be synthesized by a process shown in the following scheme 2.

Scheme 2

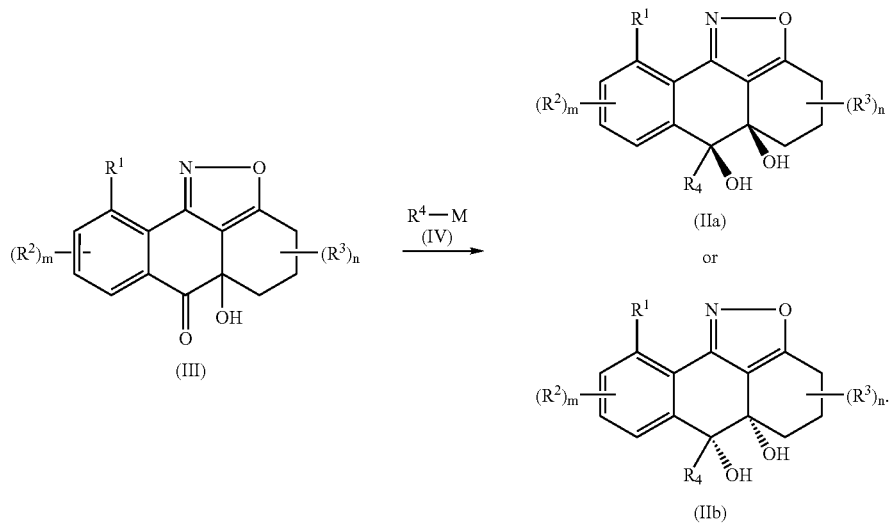

(wherein $R^1$, $R^2$, $R^3$, $R^4$, m and n show the same meanings as described above).

In the scheme 2 described above, the compound represented by Formula (IIa) or (IIb) is obtained in the form of an adduct ($R^4$) corresponding to each alkyl at a high stereoselectivity by adding alkyl metal to the compound represented by Formula (III). It can be obtained by carrying out the reaction in the absence of a solvent or in a solvent which is inactive to the reaction under the presence of $R^4$-M represented by Formula (IV). A use amount of $R^4$-M is about 2 to 5 mole, preferably about 2 to 3 mole per mole of the compound represented by Formula (III) described above.

The solvent which can be used in the above reaction and which is inactive to the reaction includes, for example, methanol, ethanol, tetrahydrofuran, diethyl ether, dichloromethane, chloroethylene, dichloroethylene, chloroform, benzene, toluene, acetonitrile, N,N-dimethylformamide and dimethyl ketone, water, 1,4-dioxane and 1,2-dimethoxyethane. They may be used by mixing two or more kinds thereof in a suitable proportion. In the reaction described above, tetrahydrofuran is preferably used for the solvent.

The reaction described above is carried out, for example, at a temperature of −120 to 40° C., preferably −100 to −20° C. for 0.01 to 5 hours, preferably 0.05 to 1 hour. This reaction is carried out usually at an atmospheric pressure, but it can be carried out, if necessary, under reduced pressure or applied pressure.

The compound represented by Formula (II) described above can be obtained, if necessary, from the reaction mixture thus obtained, for example, by separating means such as various chromatographies.

The polycyclic ketone compound of the present invention thus obtained represented by Formula (I) can be converted into useful medical compounds, agricultural chemical compounds, dye compounds and compounds for photographic materials by further chemically modifying.

EXAMPLES

The present invention shall be explained below with reference to examples. However, the present invention shall not be restricted to the examples described below.

Example 1

Synthesis of 5a-(4-methylphenyl)-10-(2,2-dimethylethyl)dimethylsilyloxy-6-oxo-3,4,5,5a-tetrahydroanthra[9,1-cd]isoxazole Ketone 3 (5a-(4-methylphenyl)-10-(2,2-dimethylethyl)dimethylsilyloxy-6-oxo-3,4,5,5a-tetrahydroanthra[9,1-cd]isoxazole) is produced by reaction shown below. That is, ketone 3 is produced through a step (first step) in which ketol 1 (10-(2,2-dimethylethyl)dimethylsilyloxy-5a-hydroxy-6-oxo-3,4,5,5a-tetrahydroanthra[9,1-cd]isoxazole) is reacted with p-tolyllithium 4 to produce diol 2 (10-(2,2-dimethylethyl)dimethylsilyloxy-5a,6-dihydroxy-6-(4-methylphenyl)-3,4,5,5a-tetrahydroanthra[9,1-cd]isoxazole) and a step (second step) in which transfer reaction of a pinacol type proceeds in diol 2 with a Lewis acid used as a catalyst to synthesize a compound in which a hydroxyl group in an internuclear position is substituted with an alkyl group.

The above two steps shall be explained below according to the following reaction formula.

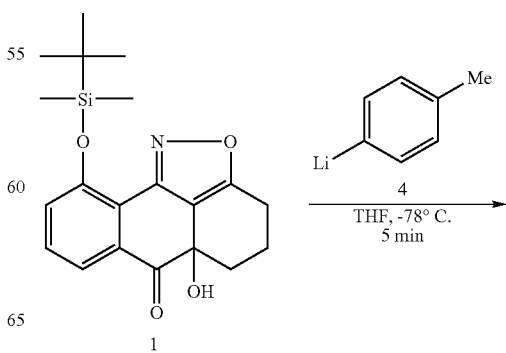

13

-continued

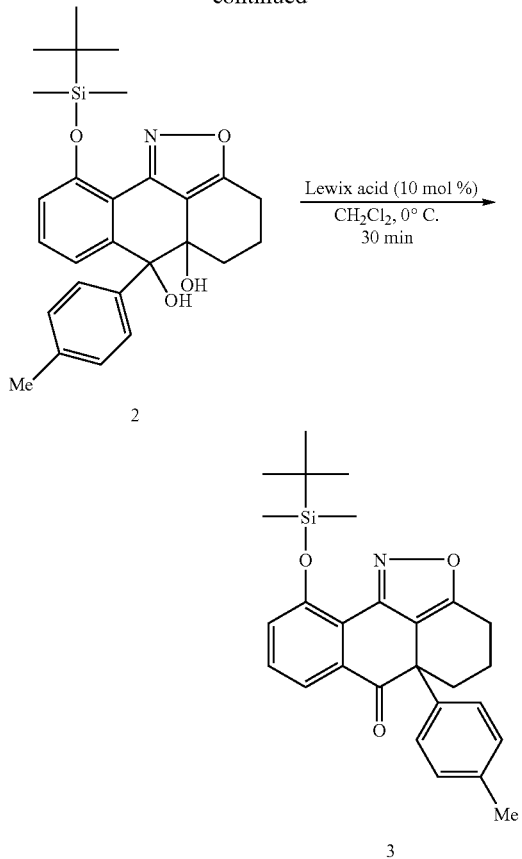

First Step

A THF solution (5.0 mL) of 4-bromotoluene (0.52 mL, d=1.39 g/mL, 4.2 mmol) was cooled to −78° C., and n-butyllithium (2.4 mL, 1.6M hexane solution, 3.8 mmol) was added thereto. The solution was stirred at the temperature which was kept intact for 20 minutes to synthesize p-tolyllithium 4. A THF solution (5.0 mL) of ketol 1 (475 mg, 1.28 mmol) was added to the above solution in 10 minutes. After stirring for 5 minutes, a saturated ammonium chloride solution was added to the reaction solution to terminate the reaction.

The product was extracted twice with ethyl acetate, and the organic layer put together was washed with a saturated saline solution and then dried on anhydrous sodium sulfate. After filtering off the drying agent, the filtrate was concentrated under reduced pressure, and the crude product thus obtained was refined by silica gel chromatography (hexane/ethyl acetate=86/14) to obtain diol 2 (546 mg, 92%) in the form of a white solid matter.

The physicochemical properties of diol 2 thus obtained are shown below.

$^1$H NMR (CDCl$_3$), 7.43 (d, 1H, J=8.0 Hz), 7.29 (t, 1H, J=8.0 Hz), 6.89 to 7.05 (m, 5H), 4.07 (s, 1H), 2.77 (dd, 1H, J=17.6, 4.7 Hz), 2.33 to 2.45 (m, 1H), 2.21 (s, 3H), 2.00 to 2.14 (m, 2H), 1.90 to 1.99 (m, 2H), 1.09 (s, 9H), 0.36 (s, 3H), 0.29 (s, 3H);

13C NMR (CDCl$_3$), 169.6, 154.7, 153.1, 147.3, 138.3, 136.8, 131.7, 128.6, 126.2, 121.4, 119.2, 116.5, 113.7, 80.7, 70.5, 28.8, 25.9, 22.2, 20.9, 18.8, 18.5, −3.9, −4.0;

Anal. calculated for C$_{27}$H$_{33}$O$_4$: C, 72.46; H, 6.08, found: C, 72.58; H, 6.21.

14

Second Step

A methylene chloride solution (1.5 mL) of diol 2 (83.1 mg, 0.1798 mmol) was cooled to 0° C., and a methylene chloride solution (0.10 mL, 0.18M, 0.018 mmol) of a boron trifluoride diethyl ether complex was slowly added thereto. The solution was stirred at the temperature which was kept intact for 30 minutes, and then a saturated sodium hydrogencarbonate aqueous solution was added to the reaction solution to terminate the reaction.

The product was extracted three times with ethyl acetate, and the organic layer put together was washed with a saturated saline solution and then dried on anhydrous sodium sulfate. After filtering off the drying agent, the filtrate was concentrated under reduced pressure, and the crude product thus obtained was refined by silica gel chromatography (hexane/ethyl acetate=90/10) to obtain ketone 3 (79.4 mg, 99%) in the form of a white solid matter.

The physicochemical properties of ketone 3 thus obtained are shown below.

$^1$H NMR (CDCl$_3$), 7.45 (d, 1H, J=8.0 Hz), 7.26 (t, 1H, J=8.0 Hz), 7.10 (d, 1H, J=8.0 Hz), 7.10 (d, 2H, J=8.1 Hz), 7.03 (d, 2H, J=8.1 Hz), 2.86 (dd, 1H, J=18.0, 6.2 Hz), 2.68 (ddd, 1H, J=18.0, 11.2, 6.6 Hz), 2.50 to 2.58 (m, 1H), 2.25 (s, 3H),1.97 to 2.05 (m, 1H), 1.90 (dd, 1H, J=13.2, 2.7 Hz), 1.52 to 1.66 (m, 1H), 1.07 (s, 9H), 0.28 (s, 3H), 0.26 (s, 3H);

13C NMR (CDCl$_3$), 198.6, 168.0, 154.0, 152.7, 137.4, 135.9, 134.5, 130.8, 129.3, 127.3, 125.4, 122.1, 120.5, 113.7, 51.4, 31.8, 25.9, 22.0, 20.9, 18.5, 18.1, −4.08, −4.13;

IR 3010, 2947, 2927, 2856, 1701, 1666, 1571, 1454, 1267, 1241, 1001, 966, 835, 811, 785, 752 cm$^{-1}$.

INDUSTRIAL APPLICABILITY

Use of the production process of the present invention makes it possible to introduce stereoselectively various substituents, and therefore capable of being provided are a useful intermediate for synthesizing medical compounds, agricultural chemical compounds, dye compounds and compounds for photographic materials and a production process for the same. Further, it can contribute as well to the field of material science.

What is claimed is:

1. A production process for producing a polycyclic ketone compound according to Formula I:

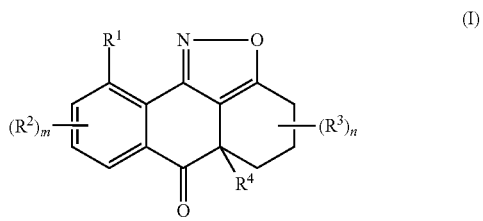

wherein R$^1$ is a hydroxyl group, a halogen atom, a silyloxy group which may be substituted, methoxy or methoxymethoxy;

R$^2$ may be independent from each other and the same as or different from each other and is a halogen atom, a hydroxyl group, a cyano group, a nitro group, an amino group, a C$_1$ to C$_3$ alkyl group or a C$_1$ to C$_3$ alkoxy group which may be substituted or two groups of R$^2$ form a condensed benzene ring together with adjacent carbon atoms;

$R^3$ may be independent from each other and the same as or different from each other and is a halogen atom, a hydroxyl group or a $C_1$ to $C_3$ alkyl group which may be substituted or two groups of $R^3$ form a condensed cyclohexyl ring together with adjacent carbon atoms;

$R^4$ is a $C_1$ to $C_3$ alkyl group which may be substituted, a vinyl group, a phenyl group or a tolyl group;

m is 0 or 1; and n is 0 or 1, wherein the compound according to Formula I is produced by subjecting a compound according to Formulae (Ia) or (IIb)

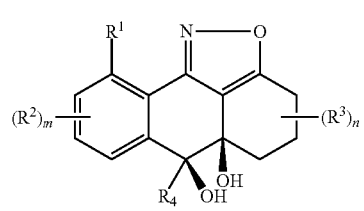

(IIa)

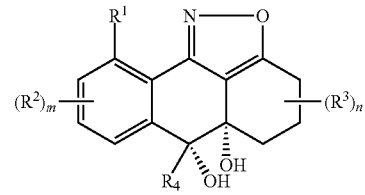

(IIb)

to acidic conditions.

* * * * *